United States Patent [19]

Barr

[11] Patent Number: 5,405,383
[45] Date of Patent: Apr. 11, 1995

[54] ARTICULATED HEART PUMP AND METHOD OF USE

[75] Inventor: Irwin R. Barr, Sparks, Md.

[73] Assignee: AAI Corporation, Cockeysville, Md.

[21] Appl. No.: 183,422

[22] Filed: Jan. 19, 1994

Related U.S. Application Data

[62] Division of Ser. No. 914,381, Jul. 14, 1992, Pat. No. 5,300,112.

[51] Int. Cl.⁶ .............................................. A61F 2/22
[52] U.S. Cl. .......................................... 623/3; 600/16
[58] Field of Search .......................... 623/2, 3, 16, 66; 600/16, 17, 18

[56] References Cited

U.S. PATENT DOCUMENTS

| | | | |
|---|---|---|---|
| 3,203,352 | 8/1965 | Schafranek | 103/87 |
| 4,625,712 | 12/1986 | Wampler | 128/1 D |
| 4,704,121 | 11/1987 | Moise | 623/3 |
| 4,817,586 | 4/1989 | Wampler | 600/16 |
| 4,846,152 | 7/1989 | Wampler et al. | 600/16 |
| 4,895,557 | 1/1990 | Moise et al. | 600/16 |
| 4,901,413 | 2/1990 | Cotherman et al. | 417/244 |
| 4,908,012 | 3/1990 | Moise et al. | 600/16 |
| 4,944,722 | 7/1990 | Carriker et al. | 600/16 |
| 4,957,504 | 9/1990 | Chardack | 623/3 |
| 4,964,864 | 10/1990 | Summers et al. | 623/3 |
| 4,969,865 | 11/1990 | Hwang et al. | 600/16 |
| 5,040,944 | 8/1991 | Cook | 415/72 |
| 5,049,134 | 9/1991 | Golding et al. | 604/151 |
| 5,092,844 | 3/1992 | Schwartz et al. | 604/151 |
| 5,300,112 | 4/1994 | Bar | 623/3 |

Primary Examiner—David Isabella
Assistant Examiner—Debra S. Brittingham
Attorney, Agent, or Firm—Howrey & Simon; Thomas J. Scott, Jr.; C. Scott Talbot

[57] ABSTRACT

An articulated, intravascular pump having multiple pump sections linked together for relative motion and driven by a common drive cable is disclosed. Each pump section is relatively short, so that it may easily pass through bends in an insertion catheter, the iliofemoral artery and the aorta artery. Disposed in the aortic arch during operation, the pump includes means for selectively directing the discharge blood flow from each pump section to inlets of major arteries branching from the arch.

8 Claims, 11 Drawing Sheets (Prior Art)
FIG. 2

ARTICULATED HEART PUMP AND METHOD OF USE

This application is a division of application Ser. No. 07/914,381, filed on Jul. 14, 1992, now U.S. Pat. No. 5,300,112.

BACKGROUND OF THE INVENTION

The invention relates to intravascular blood pumps, and specifically to such a pump having multiple, articulated pumping sections.

A common cause of death or disability from heart disease is inadequate supply of blood from an infarcted ventricle, such as caused by cardiogenic shock. If the diseased heart cannot produce a supply of blood sufficient to keep the patient alive, some form of circulatory assistance is required. Circulatory assistance can also be required in allograft cardiac replacement or heart transplants. Patients can die while waiting for transplants or while immunosuppressive agents combat the body's rejection of the transplanted heart.

Several ventricular assist devices ("VADs") have been proposed. Such devices are reviewed in the journal article Ott, Mills, Eugene, and Gazzaniga, *Clinical Choices for Circulatory Assist Devices*, XXXVI *Transactions, American Society of Artificial Internal Organs* (October/December 1990). All of the devices described in this article require major surgery for connection to the vascular system, which can involve unacceptable delay or risk for the patient.

A more acceptable approach that has been proposed, and has been used to a limited extent, is to use an intravascular blood pump. As shown schematically in FIGS. 1 and 2, such a pump 30 can be inserted into the heart 10 through the iliofemoral artery 11, aorta 12, and aortic arch 13. The pump 30 may be disposed in the aortic arch 13 or may be inserted through the aortic semilunar valve 14 into the left ventricle 15. Alternatively, the pump may be inserted into the fight ventricle 15 via the pulmonary artery 17. The pump is driven via a flexible cable 31 from an external power source 32. Blood is drawn from the left ventricle 15 into the pump in inlet flow 34 and is discharged into the aorta in discharge flow 35.

Various intravascular pumps are disclosed in the following U.S. patents:
- U.S. Pat. No. 4,625,712 to Wampler (assigned to Nimbus, Inc.) ("Wampler I");
- U.S. Pat. No. 4,817,586 to Wampler (assigned to Nimbus Medical, Inc.) ("Wampler II");
- U.S. Pat. No. 4,846,152 to Wampler, et al. (assigned to Nimbus Medical. Inc.) ("Wampler III");
- U.S. Pat. No. 4,944,722 to Carriker, et al. (assigned to Nimbus Medical, Inc.) ("Carriker");
- U.S. Pat. No. 4,964,864 to Summers, et al. (assigned to American Biomed, Inc.) ("Summers");
- U.S. Pat. No. 4,969,865 to Hwang, et al. (assigned to American Biomed, Inc.) ("Hwang"); and
- U.S. Pat. No. 5,040,944 to Cook ("Cook").

Wampler I discloses an axial-flow pump with multiple rows or rotor and stator blades. The rotor rotates at speeds in the range of 10,000 to 20,000 rpm, producing blood flows on the order of 4 liters per minute (l/min). (A healthy heart pumps blood at a rate of between 5 and 9 l/min.) It was recognized in Wampler I that pumps with such high rotational speeds have been considered unsuitable for pumping blood because the shear forces imposed on the blood in the region between the tips of the rotor blades and the stationary wall of the pump chamber can cause severe hemolysis. The solution proposed in Wampler I was to reduce the diameter of the pump chamber to thereby reduce the rotor blade tangential tip velocity and to provide a large clearance between the rotor blade tip and the pump chamber wall. The combination of these two dimensional limitations was considered to produce acceptable shear forces.

However, in Wampler III, these dimensional limitations were considered unsatisfactory. Wampler III identified the design criteria for an intravascular pump to include: a) small diameter (to readily fit into the blood vessels through which it is inserted into the heart); b) short length (to be able to follow sharp bends in the vessels); and c) a minimum number of hemolysis-producing interfaces (regions of high shear forces between rotating and stationary parts). The solution proposed in Wampler III was to use a single-stage pump, which is inherently shorter and has fewer hemolysis-producing interfaces than the multi-stage pump of Wampler I. To obtain the required pressure rise across the single stage without causing stalls or cavitation, the rotor is formed with one row producing flow that is partially axial and partially centrifugal, while the other row produces purely axial flow.

Wampler II proposes a pump design in which the diameter of the pump can be reduced without reducing the diameter of the rotor beating below the practical limits of miniaturization. The solution proposed in Wampler II is to use a screw-type axial-flow pump with a multiple-thread rotor in combination with a housing having radially-directed exit flow slots. The screw-type pump has a cylindrical pump chamber in which a screw-thread rotor rotates, rather than a multi-bladed stator. By discharging the pumped blood radially through the wall of the pump housing, rather than axially through the end of the housing, the rotor beatings can have the same diameter as the housing.

In further pursuit of a shorter pump body, with the stated goal of facilitating the passage of the pump through the bends in the insertion catheter, Carriker proposed a screw-thread type pump with radial exit slots that uses a resiliently extendable rotor extension to connect the rotor to the drive cable.

Summers identified another problem with intravascular pumps driven at high rotational velocities by a drive cable—friction between the drive cable and the wall of the insertion catheter can create hot spots in the femoral arteries. To reduce the pump operating speed, Summers proposed a pump using the moineau pump principle to deliver large volumes of blood at relatively low pressure and rotational velocity. The pump uses rotary motion to move a seal continuously through a resilient stator. Pumping action is achieved by the rotor being driven eccentrically within the stator to form a series of sealded chambers that progress axially along the pump.

In one embodiment, at the discharge end of the stator, a discharge nozzle directs the pumped blood to the intake end of a venturi tube The intake end of the venturi is also open to a chamber formed within the pump housing that communicates with the ventricle through ports in the housing. As the blood pumped by the rotor passes through the venturi, it creates a low pressure region within the venturi tube that draws blood from the chamber into the venturi to mix with the pumped blood before it is discharged from the pump. This produces a higher pumped blood volume at a lower discharge pressure.

The pump disclosed in Summers was purported to pump 3 to 4 l/min at a speed of 2,500 rpm without risk of hemoloysis because the pump had no propellers or turbine blades to produce shear forces on the blood. However, the progressive-chamber pump design requires a relatively long pump to provide adequate flow rates at the desired rotational velocity. The longer pump is more difficult to pass through bends in the insertion catheter.

Another low-rpm pump design was proposed in Hwang. The pump uses a helical-shaped foil rotating within a cylindrical housing. This pump design is purported to pump 3 to 4 l/min at 6,000 to 10,000 rpm. As with Summers, the Hwang pump is relatively long.

Finally, Cook discloses an axial flow pump in which a convoluted stationary member is mounted in a cylindrical housing. A pair of spiral impeller rods are rotatably disposed between the stationary member and the internal wall of the housing and are driven by a conventional drive cable. Again, the pump disclosed is relatively long—1.25" (30 mm)—with a diameter of 0.25" (6 mm) and operates at high speeds—approximately 20,000 rpm.

Figure 1:
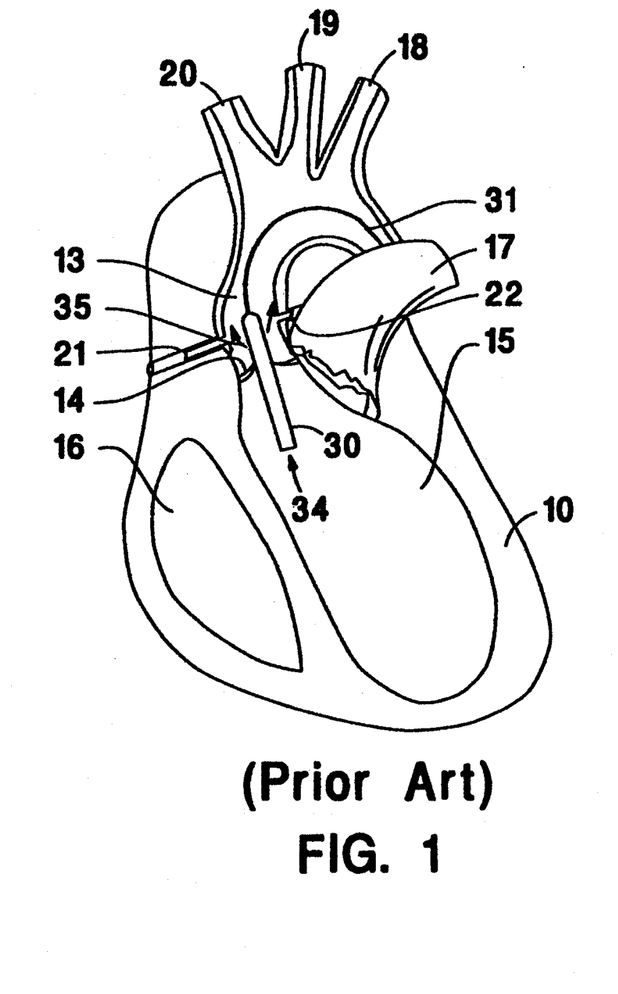
FIG. 1 is a schematic illustration of a heart, showing the aortic arch and major arteries, and showing a prior art pump disposed within the left ventricle and aortic arch.
Figure 2:
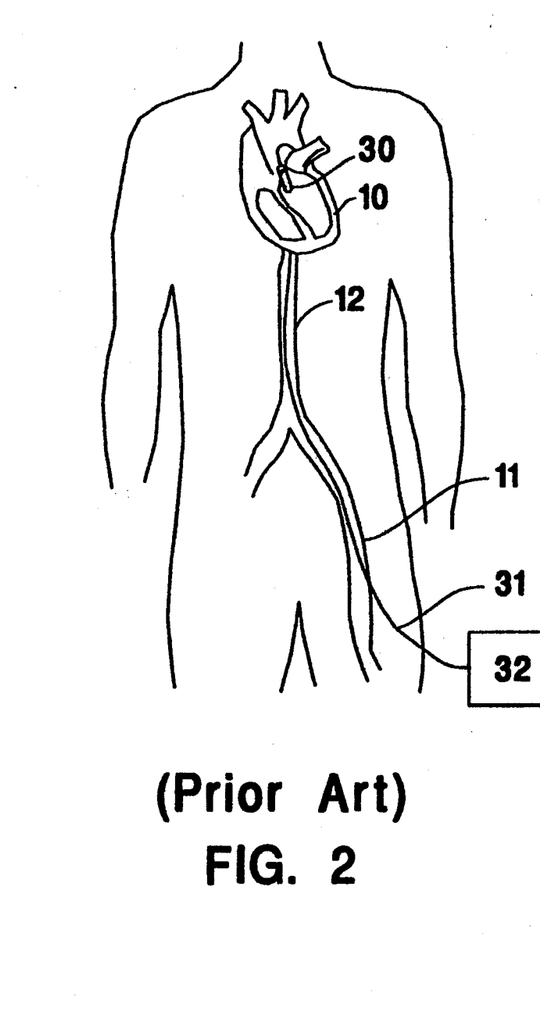
FIG. 2 is a schematic illustration of the route by which a prior art intravascular pump is inserted into the heart.

Another disadvantage shared by all of these pump designs is that they do not allow the pumped blood to be preferentially directed. As shown in FIG. 1, three major arteries branch from the aortic arch 13: the left subclavian artery, 18, the left common carotid artery 19, and the brachiocephalic artery 20. In addition, the coronary arteries 21 and 22, which supply blood to the heart muscle itself, branch from the aortic arch just downstream of the aortic valve 14. It is desirable to preferentially direct some of the discharge blood flow 35 from the pump into the entrances of these arteries. Such directional treatment maximizes the effectiveness of the energy conveyed to the blood from the pump (i.e., minimal energy is wasted through the use of aortic arch walls to redirect discharged blood). As such, the overall efficiency of the pump is enhanced. Further, directional treatment into multiple arteries provides a more uniform and equitable distribution of blood leaving the heart. However, the pump designs described above simply discharge blood along or about the axis of the aorta, with no preferential orientation.

SUMMARY OF THE INVENTION

The drawbacks of the intravascular pump designs described above are overcome by the method and apparatus of the invention. The intravascular pump is articulated, having multiple pump sections linked together for relative motion and driven by a common drive cable. Each pump section is relatively short, so that it can pass easily through bends in the insertion catheter, the iliofemoral artery and the aorta artery. While a single pump section could not provide an adequate flow rate at a rotational velocity sufficiently low to avoid blood hemolysis, multiple pump sections can do so. By linking the sections for relative motion, the pump can pass easily though the catheter.

Disposed in the aortic arch during operation the pump includes means for selectively directing the discharge blood flow from each section to the inlets of the major arteries branching from the arch.

DETAILED DESCRIPTION

Figure 3:
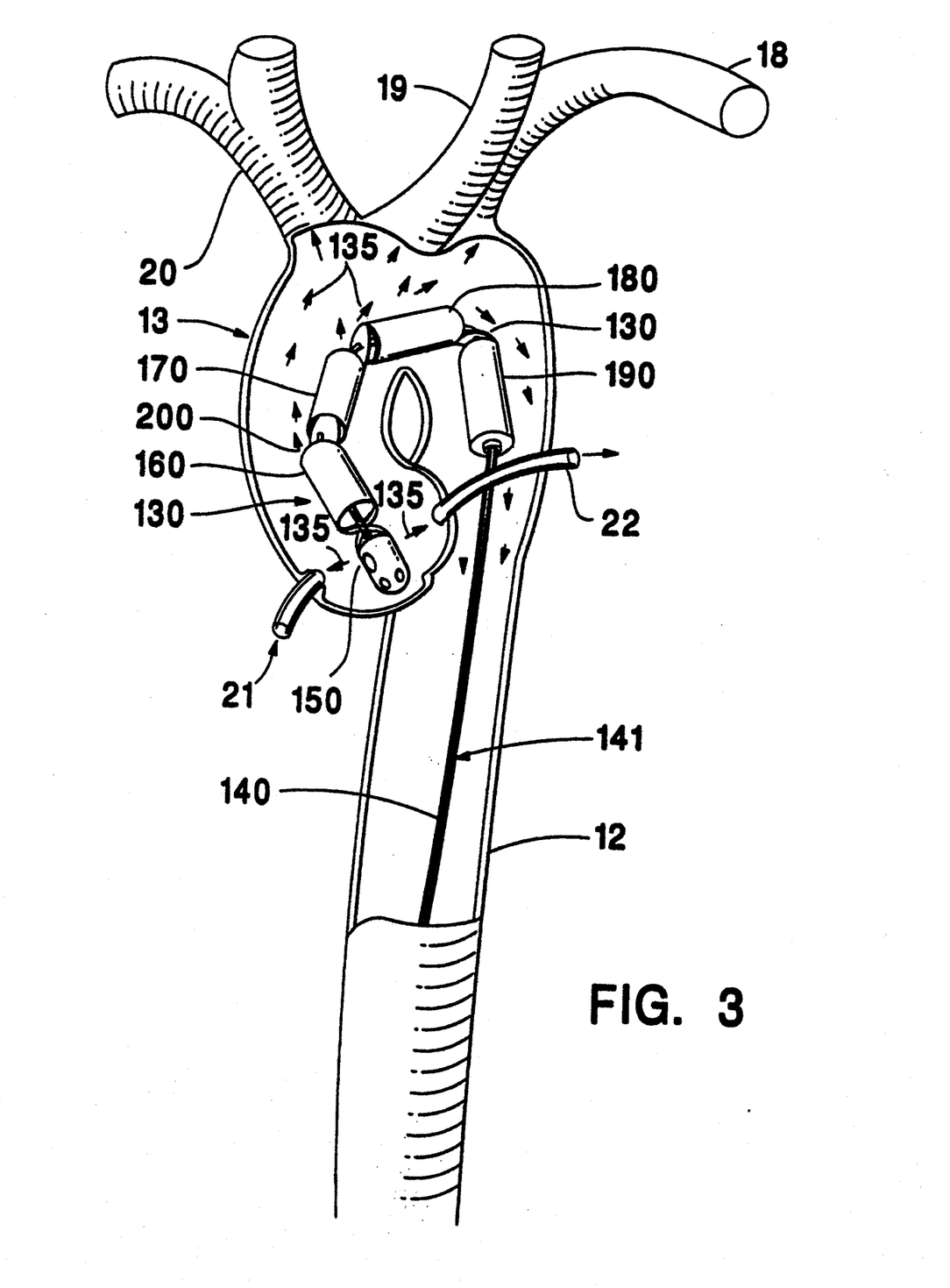
FIG. 3 is a partial perspective view of a heart showing the aortic arch and major arteries and showing an intravascular blood pump constructed according to the principles of the invention disposed within the aortic arch.

Like the prior-art intravascular pumps discussed above, the invention disclosed herein operates in aortic arch 13, as shown generally in FIG. 3. Multiple pump sections 150-190 interconnected with articulated links 200 provide sufficient flexibility for pump 130 to navigate the aorta and iliofemoral arteries during installation, and ultimately fit within the confines of arch 13 during operation. The flexibility provided by the articulated links need only be off of a single plane (i.e., two directions located 180° apart) as the pump may be rotated during installation to provide maximum flexibility in the direction of the arterial bends.

Pumping is achieved through the rotation of impellers or rotors located within each pump section. The impellers are driven by a single, flexible drive cable 140 housed within teflon sleeve 141. As in the prior art, cable 140 traverses the length of the aorta and iliofemoral arteries, driven by an external power source.

As detailed in FIG. 3, articulated links 200 enable each pump section housing to be relatively positioned so to direct discharge flow 135 away from inlets of pump sections located further downstream and towards a variety of arterial inlets branching off the arch (i.e., the left subclavian artery 18, the left common carotid artery 19, the brachiocephalic artery 20, the coronary arteries 21 and 22, and the aorta itself 12). The effectiveness of such positioning may be augmented by the angular orientation of the articulated link and/or the particular configuration of the pump section outlet, as discussed below.

To maintain proper orientation between each pump section housing and the foregoing arterial inlets, the housings may be secured to a stationary object relative to the rotational motion of cable 140. Typically, such object will be teflon sleeve 141 which extends the full length of cable 140 and may be fixedly anchored to a stationary object outside the body. As all pump section housings, in such instances, are secured to the same stationary object (either directly or indirectly through another section), the orientation between each section also remains fixed. Alternatively, proper orientation may be maintained by resting one or more pump housing sections on the inner wall of the aortic arch and relying on friction to impede any rotational motion of each pump section housing during operation.

Thus, an intravascular blood pump constructed according to the principles of the invention includes several fundamental elements. First, the articulated link interconnecting two pump sections should be flexible off of at least one plane (i.e., flexible in two directions 180° apart) to enable an elongate assembly to navigate the iliofemoral and aorta arteries during installation and to effectively direct blood within the aortic arch during operation.

Second, the inlets and outlets of each pump section should be oriented to minimize the flow of blood from an upstream section outlet to a downstream section inlet. Concurrently, the outlets should be configured to direct discharged blood towards arterial inlets located within the aortic arch.

Third, means must be provided to isolate each pump section from the rotational motion of the drive cable used to rotate the impellers of the pump while maintaining a fixed angular relationship among and between each pump section.

Reference will now be made in detail to several embodiments of the invention, examples of which are illustrated in the accompanying drawings, to further describe the invention.

1. Embodiments

A first, and preferred, embodiment of the invention is illustrated in FIGS. 4–11. The pump 230 is shown with five pump sections 250, 260, 270, 280 and 290, and sleeve-stop 300. Pump section 250 contains a plurality of inlets 310 and outlets 313 located on the sides of teflon, pump-section housing 370. These inlets and outlets are disposed near the front and midpoint, respectively, of the section. Outlets 313 are designed to direct blood into the inlets of the coronary arteries, identified as elements 21 and 22 in FIG. 3. In contrast, each of sections 260–290 have a single inlet 312 and outlet 311 disposed at the ends of each teflon housing 350. Outlets 311, as discussed below, direct blood into and through the portions of aortic arch 13 downstream of the coronary arteries.

Figure 9:
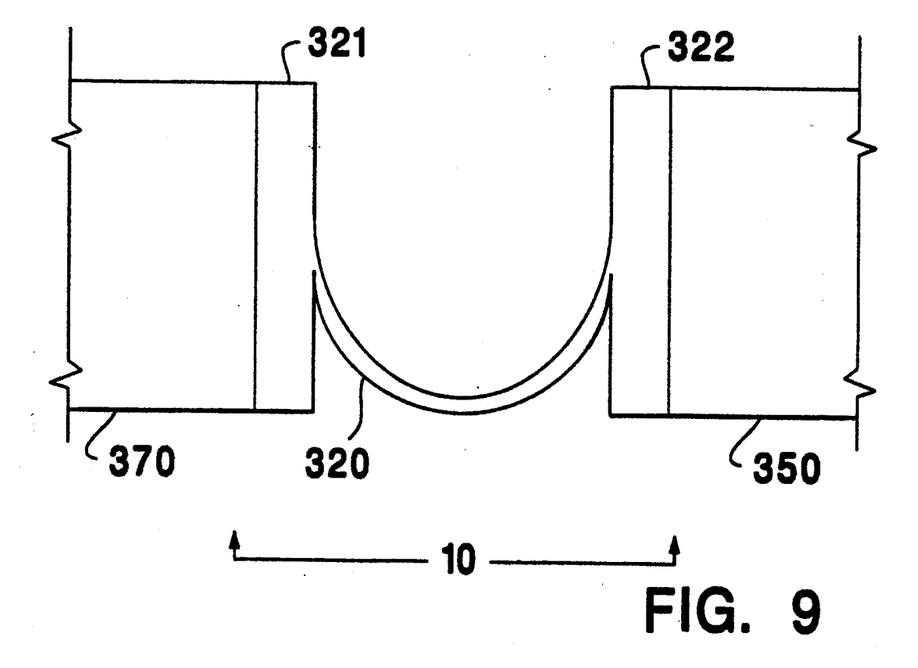
FIGS. 9 and 10 are partial schematic side views of a criss-cross articulated link interconnecting two pump sections of the first embodiment.
Figure 10:
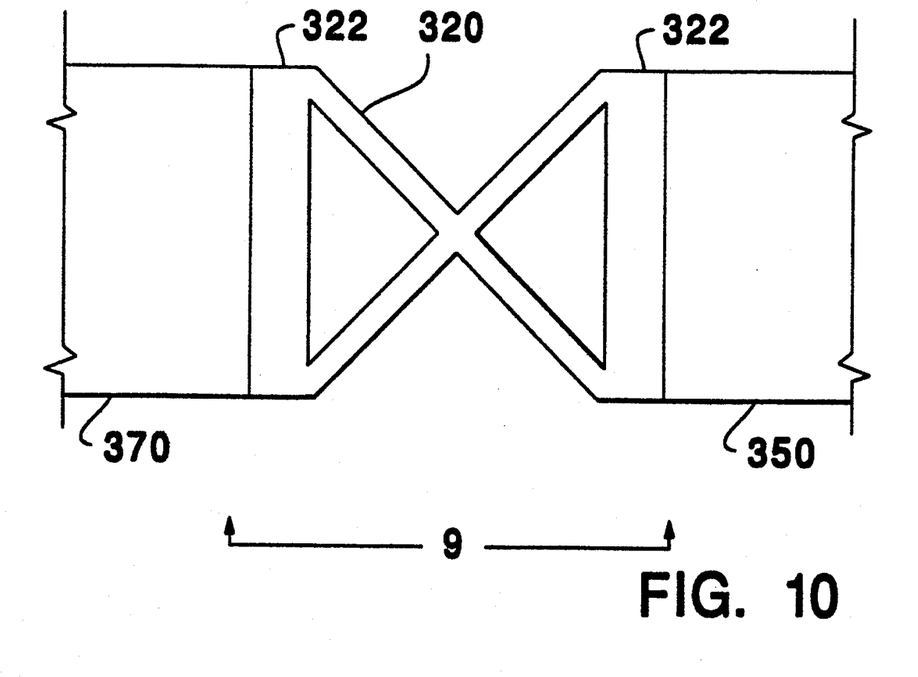

Sections 250 and 260 are interconnected by means of criss-cross link 320, shown in detail in FIGS. 9 and 10. This link provides limited flexibility and no guidance to blood discharged from section 250 since the corresponding outlets are disposed on the side of the pump section housing. As shown in FIGS. 9 and 10, link 320 is integrally formed with two pump section mounting portions 321 and 322. Portion 321 provides a solid, short male insert (approximately 1/6th the length of housing 370) which rests inside housing 370 and is secured to the inner walls of the housing by a suitable adhesive, or other means. This insert contains a passage large enough for cable 140 to pass through. Portion 322 provides a hollow, cylindrical insert which extends the length of housing 350 and is secured to the inner walls of the housing by a suitable adhesive, or other means. This insert forms a double wall with housing 350 that is sufficiently wide to accommodate impeller 340.

Figures 4, 5, 6:
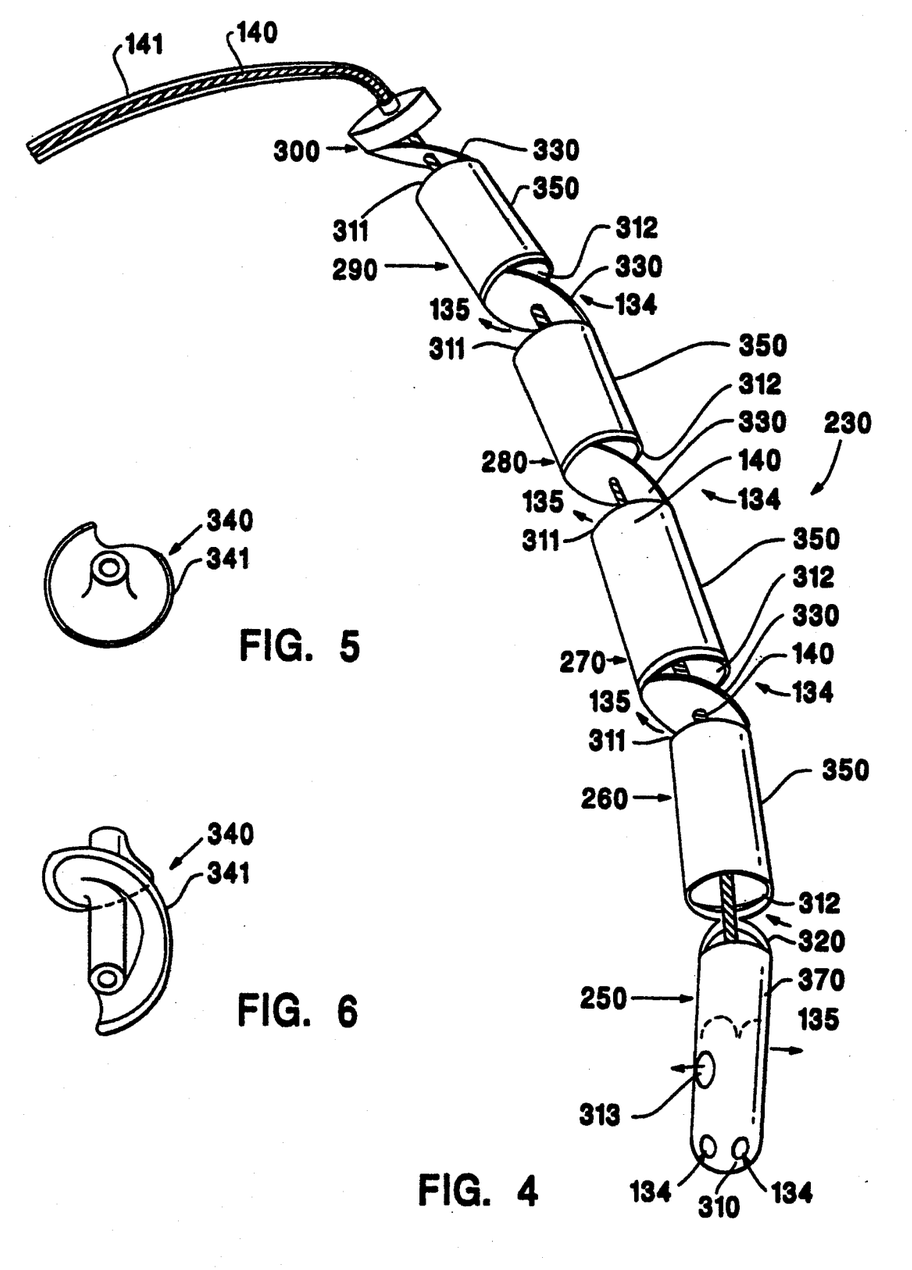
FIG. 4 is a partial perspective view of a first embodiment of an intravascular blood pump constructed according to the principles of the invention.
FIG. 5 is a plan view of a single-thread impeller.
FIG. 6 is a perspective view of a single-thread impeller.
Figure 7:
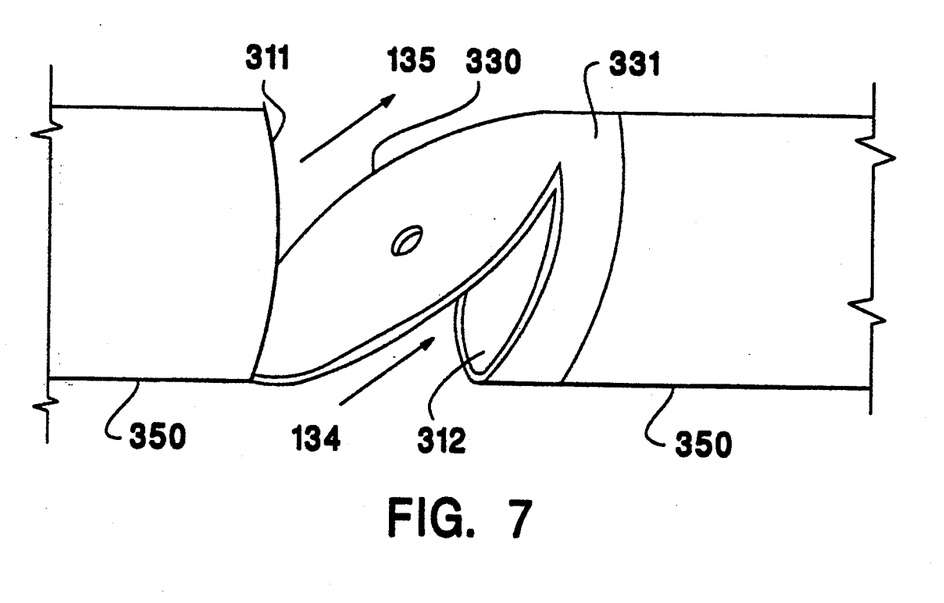
FIG. 7 is a partial perspective view of an angular articulated link interconnecting two pump sections of the first embodiment.
Figure 8:
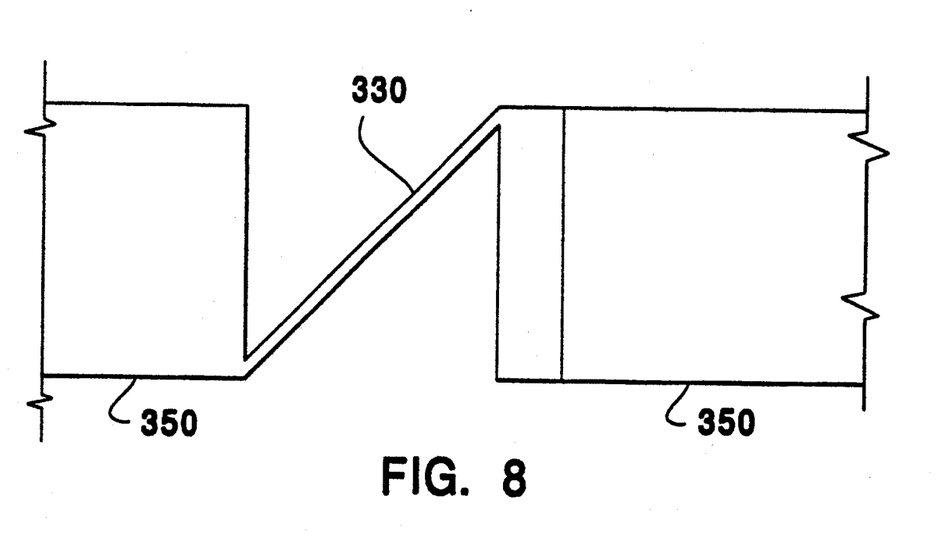
FIG. 8 is a partial schematic side view of an angular articulated link interconnecting two pump sections of the first embodiment.

Remaining sections 260–290 and stop 300 are interconnected by means of angular link 330, which has greater flexibility than link 320 and guides blood entering and exiting each section. As shown in FIGS. 4, 7 and 8, each link 330 creates a barrier between blood entering the inlet 312 of the downstream pump section and blood exiting the outlet 311 of the upstream pump section. Exiting blood 135 is directed away from entering blood 134, enabling the multiple pump sections to operate in parallel on different portions of a single blood stream exiting the heart. When properly installed within aortic arch 13, link 330 is disposed so that discharge flow 135 is directed towards the aortic arch cavity downstream of the coronary artery. Accordingly, this link in combination with the relative position of each section within the arch provides a directed discharge flow away from the inlets of downstream pump sections and towards the various arterial inlets branching from the aortic arch, as shown generally in FIG. 3.

As shown in FIGS. 7 and 8, link 330 is integrally formed with housing 350 at exit 312 and pump section mounting portion 331. Like portion 322, portion 331 provides a hollow, cylindrical insert which extends the length of housing 350 and is secured to the inner walls of the housing by a suitable adhesive, or other means. This insert forms a double wall with housing 350 that is sufficiently wide to accommodate impeller 340.

Figure 11:
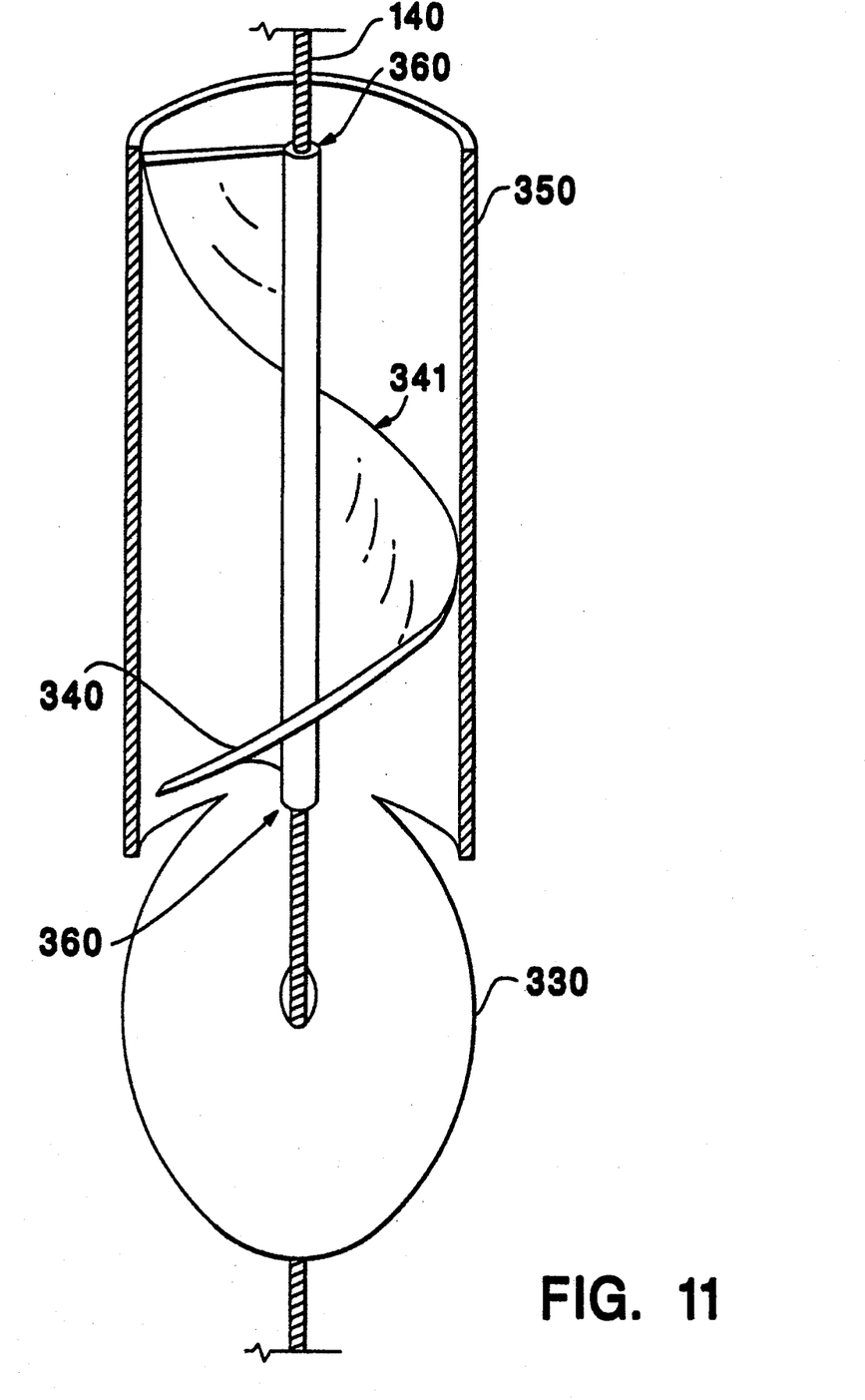
FIG. 11 is a partial schematic sectional view of a pump section and angular articulated link of the first embodiment.

Each pump section contains a nylon, left-handed, single-thread impeller 340, shown in detail in FIGS. 7, 8 and 11. Impeller 340 is secured to cable 140 by a suitable adhesive, such as cyanoacrylate glue 360, or other means. Blood is drawn into the inlets and discharged from the outlets of each section as a result of the rotation of this impeller. The pitch of impeller 340 is tailored to the length of the section in which it resides so that thread crest 441 traverses the length of its corresponding pump section in one rotation. Although pump sections 250–290 each measure 0.75 inches in length, the presence of side-mounted inlets 310 on section 250 shortens the enclosed pumping chamber of this section to 0.3125 inches. Accordingly, the pitch of impeller 340 for section 250 is 0.3125 inches while the pitch of the impellers for the remaining sections is 0.75 inches.

The inner diameter of each pump section (260–290) containing the hollow cylindrical insert of pump section mounting portion 331 is approximately 0.255 inches. The outer diameter of each impeller 340 contained within the foregoing sections is approximately 0.252 inches. Accordingly, impeller 340 operates with a clearance of approximately 0.003 inches.

Employing an impeller with a pitch approximately equal to the length of the pump section (or for section 350, the length of the enclosed pumping chamber) maximizes blood throughput for each rotation. Not only does blood traverse the section in a single rotation, but the quantity of the traversing blood is increased since a minimum number of threads occupy space inside each section.

Referring to FIGS. 4 and 11, flexible cable 140 passes through interconnected pump sections 250-290 and collectively rotates separate impellers contained within each section. This cable is constructed from seven course strands of steel wound about a central axis. Each course strand comprises 7 fine strands of steel. The resulting assembly, having a diameter of approximately 1/32 of an inch, is typically identified as "aircraft stainless steel cable."

Relative segment position on cable 140 is provided by links 320 and 330 which maintain a pre-determined distance between each segment and stop 300. The cable itself is held within pump assembly 230 by the restricted mobility of the impellers to which the cable is glued.

Teflon sleeve 141, which encases cable 140 as it traverses the aorta and iliofemoral arteries, terminates at stop 300, as illustrated in FIG. 4. This sleeve serves as a means for isolating pump assembly 230 from the rotational movement of cable 140 by being secured to both stop 300 and an external object that is stationary relative to the rotation of cable 140, such as the housing of the drive motor.

Figure 12:
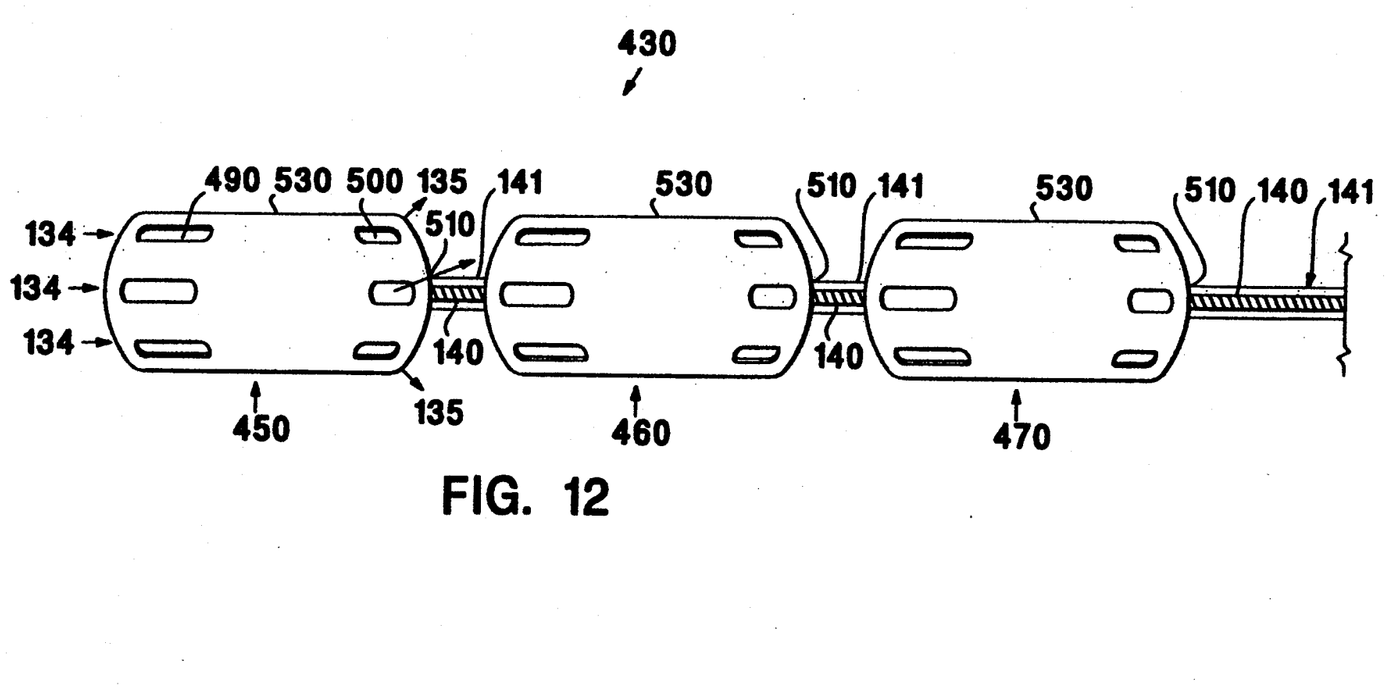
FIG. 12 is a schematic side view of a second embodiment of an intravascular blood pump constructed according to the principles of the invention.
Figure 13:
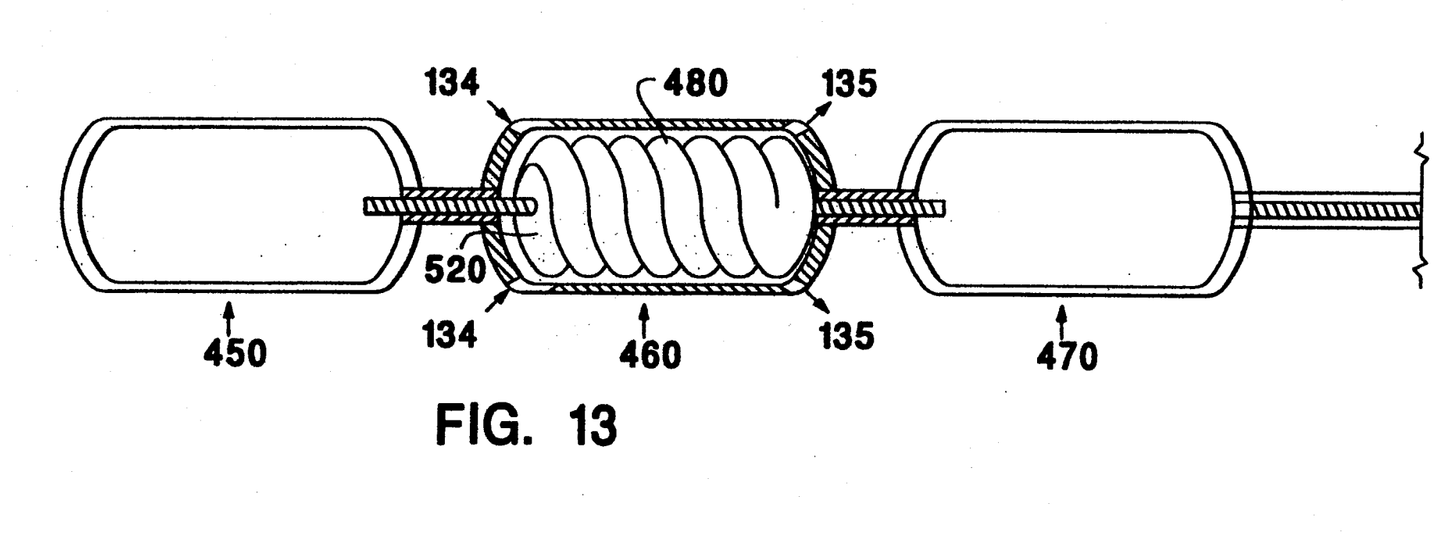
FIG. 13 is a schematic sectional view of a second embodiment of an intravascular blood pump constructed according to the principles of the invention revealing a multi-threaded impeller.

A second embodiment of the invention is illustrated in FIGS. 12 and 13. The pump 430 is shown with three pump sections 450, 460, and 470. Each pump section contains a plurality of inlets 490 and outlets 500 on each teflon housing 530 to accommodate the flow of blood. As seen most clearly in FIG. 13, the inlets and outlets are angled to avoid a straight path of blood from the output of an upstream pump to the input of a downstream pump (i.e., sections 450 and 460, respectively). These outlets may also contribute to the direction of discharge flow 135 towards the arterial inlets of aortic arch 13 when the segments are disposed within the arch in a manner similar to that illustrated in FIG. 3.

Although not shown in FIGS. 12 and 13, one pump section may contain additional outlets to direct blood into the intakes of the coronary arteries, identified as elements 21 and 22 in FIGS. 1 and 3. Such outputs would be disposed perpendicularly to the longitudinal axis of the pump section like outlets 313 of segment 250 in the first embodiment.

Figure 14:
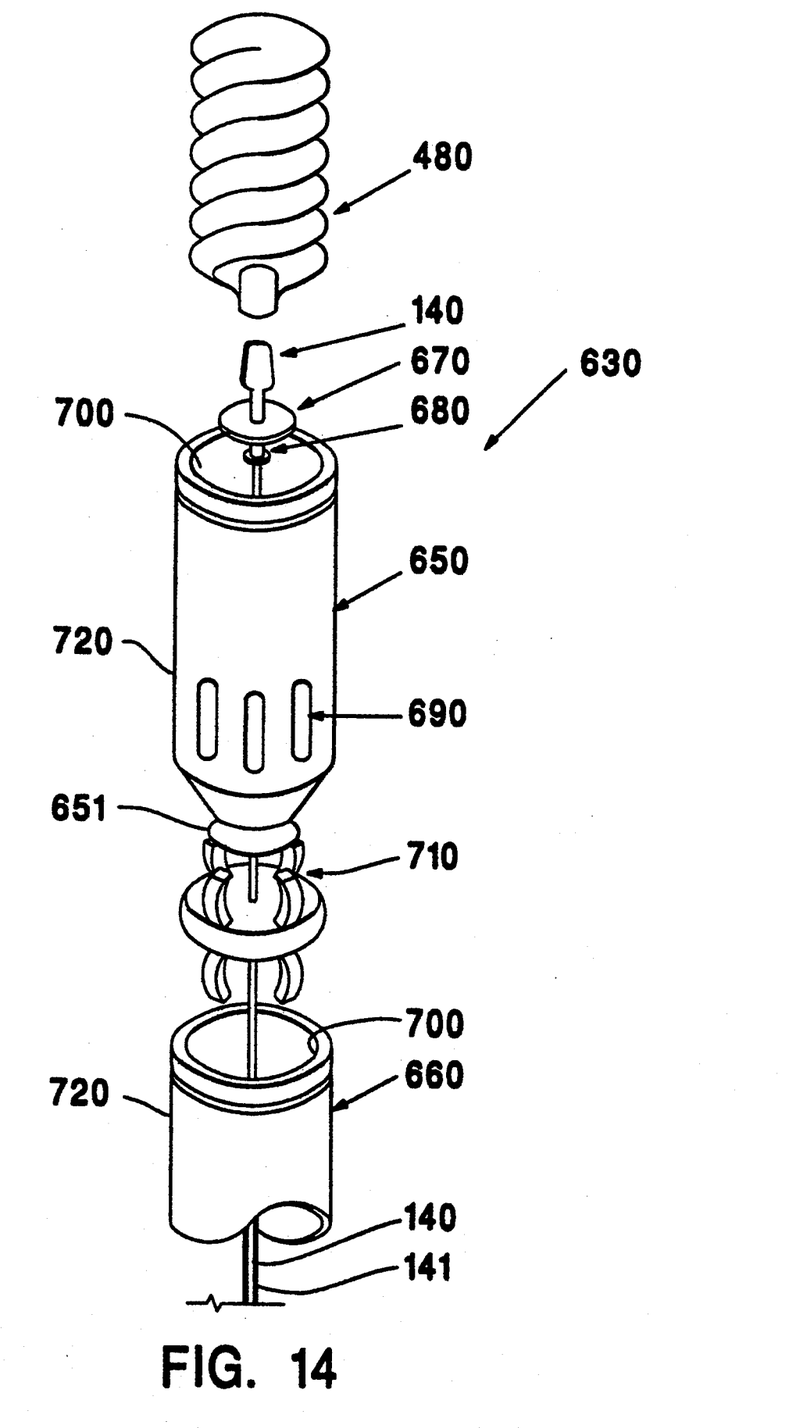
FIG. 14 is a partial perspective view Of a third embodiment of an intravascular blood pump constructed according to the principles of the invention.

Within each section lies a nylon, multiple-thread impeller 480 fixedly secured to cable 140 by a suitable adhesive, such as cyanoacrylate glue 520, or other means. Blood is drawn into inlets 490 and discharged via outlets 500 from the rotation of this impeller. To reduce the possibility of rotational slippage, that portion of cable 140 upon which impeller 480 rests may be flattened, as shown in FIG. 14. Impeller 480 is designed to pump a maximum displacement of blood per revolution. Alternatively, a multiple bladed turbine may also be used.

As in the first embodiment, a flexible cable 140 encased within teflon sleeve 141 interconnects the pump sections and collectively rotates separate impellers contained within each section. The cable itself is held within pump assembly 430 by the restricted mobility of the impellers to which the cable is secured.

Relative section position on cable 140 is maintained by teflon sleeve 141 which has a larger diameter than the section hole(s) 510 through which the cable passes. Accordingly, the sleeve properly interspaces the sections as well as maintains their position at one end of the cable. Additionally, the sleeve serves as a means for isolating the pump section housings from the rotational movement of cable 140 by being fixedly secured to both these housings as well as an external object which is stationary relative to the rotation of cable 140.

A third embodiment of the invention is detailed in an exploded view in FIG. 14. As in the previous embodiment, pump 630 includes multiple pump sections interconnected by an articulated link. As shown in FIG. 14, a typical section 650 contains a teflon housing 720 with a single inlet 700 and a plurality of outlets 690. Although some discharge may escape through the cable hole located in the base of 720, the amount should be minimal since lock nut 680 and washer 670 rest on top of the hole. The outlets 690 are angled for reasons noted above.

Like the second embodiment, pump 630 employs a multiple-thread impeller 480 connected to cable 140 as described above. The cable maintains its position within each section by means of lock nut 680 resting against the section base.

Figure 15:
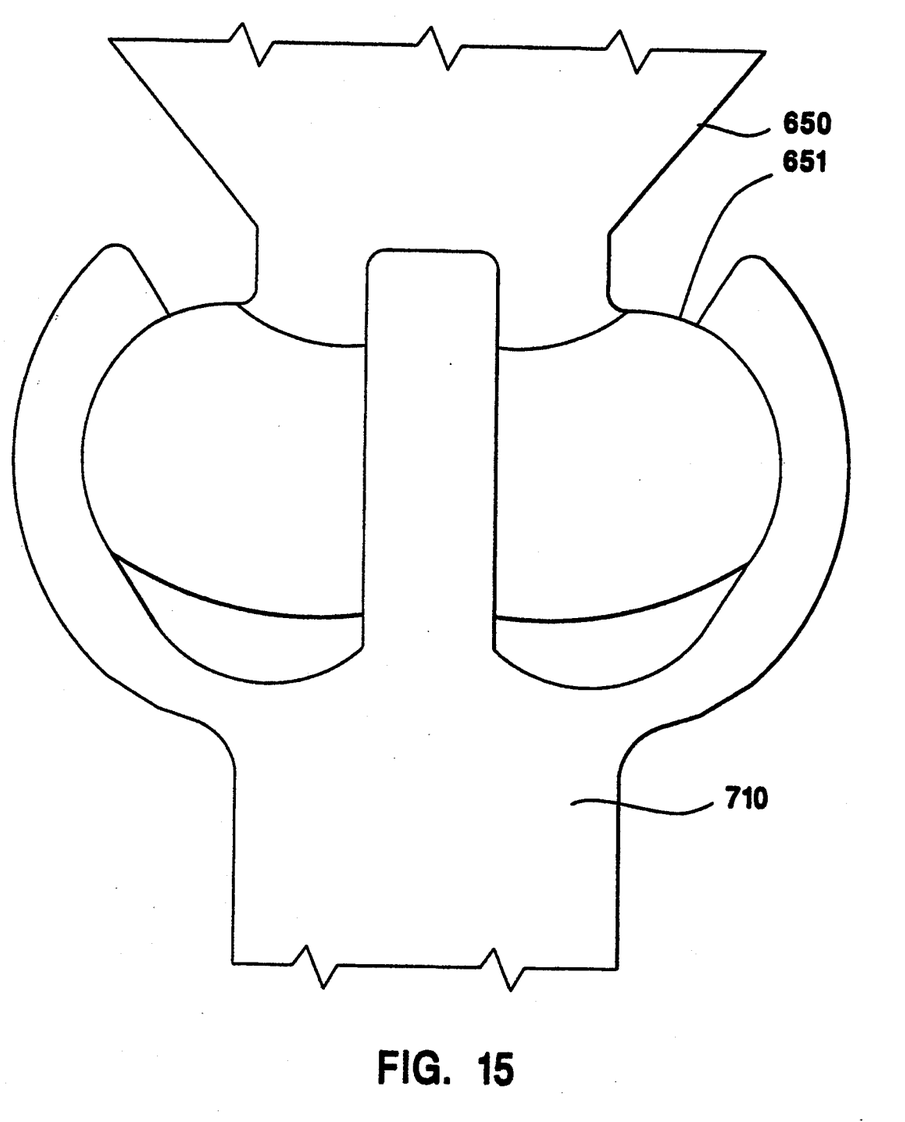
FIG. 15 is a front view of the articulation link of the third embodiment.

Pump sections are interconnected by means of an articulated "snap-on" link 710 as illustrated in FIGS. 14 and 15. This joint snaps over ridge 651 of housing 720 and provides for limited flexibility in all directions from the longitudinal axis of the section.

Unlike the previous two embodiments, housings 720 of pump 630 are not fixedly secured to a stationary object relative to the rotation of cable 140. Rather, one or more of these housings rest on an inner wall of the aortic arch during operation, relying on friction to impede any rotational motion of such housings. Those housings not in direct contact with the aortic wall may rely on friction present in the connection of link 710 to indirectly restrain any rotational motion.

2. Operation

The proper orientation of an articulated heart pump is shown generally in FIG. 3. As noted above, the angled links of the first embodiment or the angled outlets of the second and third embodiments in conjunction with the relative position of the pump sections in the aortic arch provide the necessary combination to direct the blood towards desired arterial inlets.

Regarding the first, and preferred, embodiment, pumping volumes of approximately 0.57 l/min out of section 250 into the coronary arteries, and approximately 5-6 l/min out of the combined outputs of sections 260-290 into the aortic arch have been achieved at impeller rotational speeds of approximately 12,000 to 15,000 rpm. Of course, the effectiveness of this pumping volume is enhanced by the directed discharge flow of each pump section into the appropriate arterial inlet of the aortic arch.

During the course of experimentation with pump 230, cable 140 was found to kink when rotated in the direction of the twist of its strands, that is, the direction that tightens the cable. Accordingly, in a preferred operation, cable 140 should be rotated in the direction opposite to the twist of its strands, that is, the direction that loosens the cable. In such an operation, cable 140 is held together by teflon sleeve 141.

As disclosed in the foregoing embodiments, pump section housings and impellers may be constructed from teflon and nylon, respectively. These materials are chosen for their compatibility with blood, resistance to corrosion by blood and low operating friction. Any other material with similar characteristics may also be employed in the construction of these components of the invention.

Figure 16:
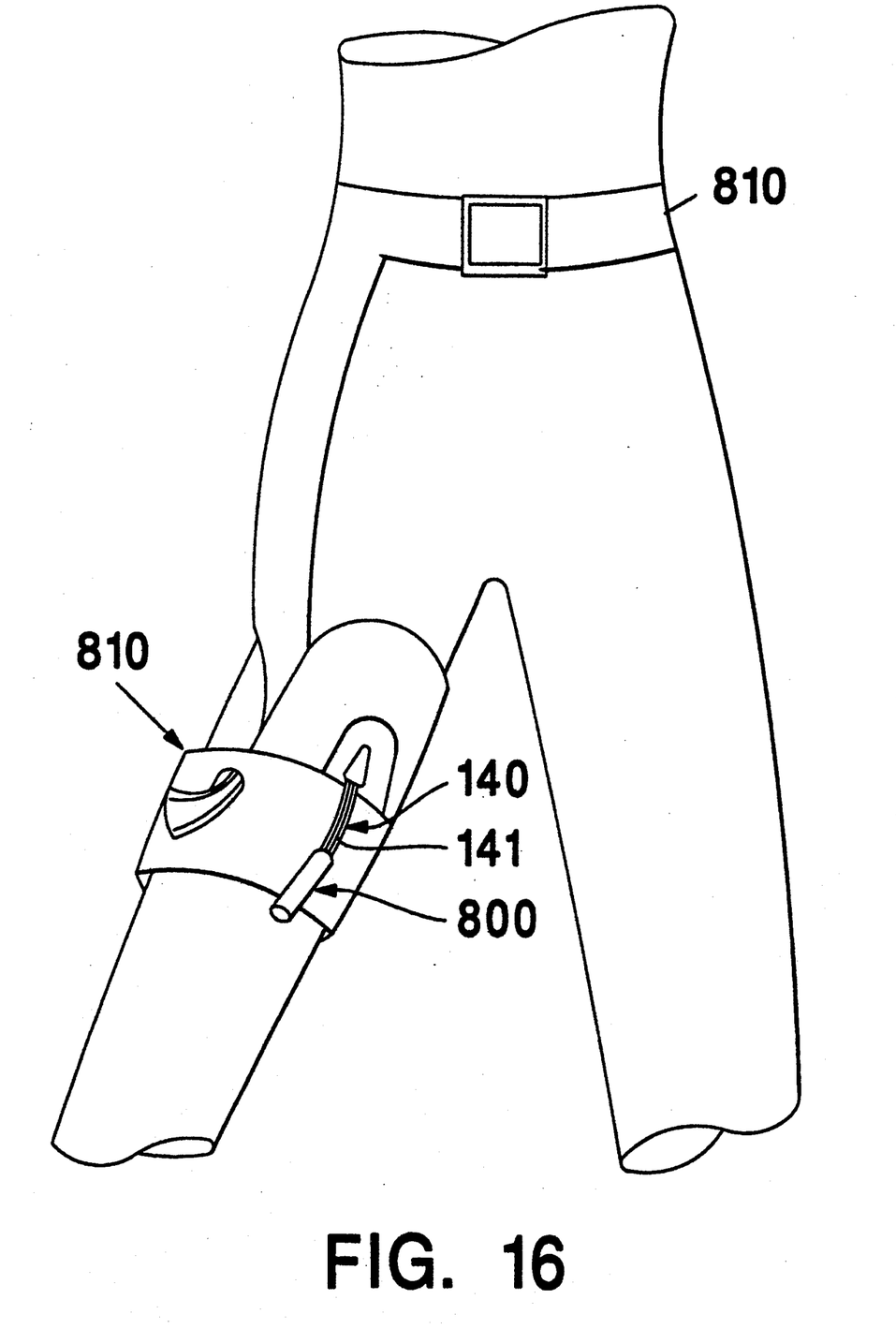
FIG. 16 is a partial view of a user body showing the external pump power source secured to the body by a support belt.

As shown in FIG. 16, the external power source used to drive cable 140 may be motor 800 secured to the user by means of support belt 810.

When used for the first time, the intravascular blood pump can be brought up to speed very slowly to avoid shock. Once in operation, the system can use the same instrumentation now available with certain catheters to transmit blood pressure, heart rate and rpm, thereby providing sufficient information for feedback control.

What is claimed is:

1. A method of augmenting the flow rate of blood from a heart comprising the steps of:
   a. inserting into an artery an intravascular pump comprising:
      i. first and second pump sections, each pump section having:
         (1) a housing having an inlet and an outlet; and
         (2) an impeller rotatably mounted within said housing;
      ii. a link member coupled to said first pump section and to said second pump section and permitting relative movement of said first and second pump sections; and
      iii. a flexible drive member coupled to said impeller contained in each of said first and second pump sections;
   b. moving said first and second pump sections along said artery until said pump sections are disposed adjacent the outlet of a ventricle of the heart: and
   c. rotating said impellers with said flexible drive to draw blood into said inlet of each of said housings and discharge the blood from said outlet of each of said housings.

2. The method of claim 1, further comprising the step of directing the blood discharged from said outlet of one of said housings toward an artery branching from the vessel in which said intravascular pump is disposed.

3. The method of claim 2 wherein said intravascular pump is disposed in the aortic arch and adjacent the left ventricle of the heart.

4. A circulatory assist system for use in a patient comprising:
   a. an intravascular pump having:
      i. first and second pump sections, each pump section having:
         (1) a housing having an inlet and an outlet; and
         (2) an impeller rotatably mounted within said housing; and
      ii. a link member coupled to said first pump section and to said second pump section and permitting relative movement of said first and second pump sections;
   b. a drive member coupled to said impeller contained in each of said first and second pump sections;
   c. a motor for rotating said drive member;
   d. an insertion catheter for connection to an artery and providing a passage for said drive member into the artery; and
   e. means for securing said insertion catheter and said motor to the patient.

5. The circulatory assist system of claim 4 wherein said impeller is a screw thread impeller.

6. The circulatory assist system of claim 4 wherein said impeller is a bladed turbine rotor.

7. The circulatory assist system of claim 4 further comprising means for directing the flow of blood discharged from said outlet of said housing of said first pump section.

8. The circulatory assist system of claim 7 wherein said directing means is disposed on said link member.

* * * * *